(12) United States Patent
Yamada et al.

(10) Patent No.: US 11,406,785 B2
(45) Date of Patent: Aug. 9, 2022

(54) GAS PRODUCT, METHOD FOR PRODUCING SAME AND METHOD FOR PRODUCING MEDICAL INHALATION GAS

(71) Applicants: SUMITOMO SEIKA CHEMICALS CO., LTD., Hyogo (JP); The Kitasato Institute, Tokyo (JP)

(72) Inventors: Masaaki Yamada, Yachiyo (JP); Ichiro Misawa, Tokyo (JP); Hirosuke Kobayashi, Tokyo (JP); Kenichi Kokubo, Sagamihara (JP)

(73) Assignees: SUMITOMO SEIKA CHEMICALS CO., LTD., Hyogo (JP); THE KITASATO INSTITUTE, Tokyo (JP)

(*) Notice: Subject to any disclaimer, the term of this patent is extended or adjusted under 35 U.S.C. 154(b) by 0 days.

(21) Appl. No.: 17/285,788

(22) PCT Filed: Mar. 4, 2020

(86) PCT No.: PCT/JP2020/009238
§ 371 (c)(1),
(2) Date: Apr. 15, 2021

(87) PCT Pub. No.: WO2020/184345
PCT Pub. Date: Sep. 17, 2020

(65) Prior Publication Data
US 2021/0308412 A1    Oct. 7, 2021

(30) Foreign Application Priority Data
Mar. 13, 2019  (JP) .............................. JP2019-045754

(51) Int. Cl.
*A61M 16/12* (2006.01)
*A61M 16/10* (2006.01)
*F17C 5/06* (2006.01)

(52) U.S. Cl.
CPC .......... *A61M 16/12* (2013.01); *A61M 16/101* (2014.02); *F17C 5/06* (2013.01);
(Continued)

(58) Field of Classification Search
CPC ................ A61M 16/12; A61M 16/101; A61M 2202/0208; A61M 2202/0266;
(Continued)

(56) References Cited

U.S. PATENT DOCUMENTS 4,387,082 A    6/1983 Grosskinsky et al.
5,826,632 A *  10/1998 Micke ....................... F17C 5/06
141/9

(Continued)

FOREIGN PATENT DOCUMENTS

CN    102883730    1/2013
CN    104857034    8/2015
(Continued)

OTHER PUBLICATIONS

International Search Report of PCT/JP2020/009238, dated Apr. 21, 2020, 3 pages.
(Continued)

*Primary Examiner* — Reinaldo Sanchez-Medina
*Assistant Examiner* — Stephanie A Shrieves
(74) *Attorney, Agent, or Firm* — Hamre, Schumann, Mueller & Larson, P.C.

(57) ABSTRACT

An aspect of the present invention is a gas product including: a gas container; and a gas composition filled in the gas container, in which the gas composition includes nitrogen monoxide, hydrogen, and an inert gas, and a concentration of the nitrogen monoxide is 20% by volume or less based on a volume of the gas composition.

2 Claims, 1 Drawing Sheet

(52) U.S. Cl.
CPC ............... *A61M 2202/0208* (2013.01); *A61M 2202/0266* (2013.01); *F17C 2221/012* (2013.01); *F17C 2221/014* (2013.01); *F17C 2223/0123* (2013.01)

(58) Field of Classification Search
CPC ....... A61M 2202/0275; A61M 15/0003; F17C 5/06; F17C 2223/0123; F17C 2221/014; F17C 2221/012; Y02E 60/32; A61P 9/10; A61P 43/00; A61K 33/00
USPC .......................................................... 141/18
See application file for complete search history.

(56) References Cited

U.S. PATENT DOCUMENTS

| | | | | |
|---|---|---|---|---|
| 7,955,294 | B2* | 6/2011 | Stenzler | A61M 16/122 604/23 |
| 8,636,040 | B2* | 1/2014 | Deck | G05D 11/132 141/54 |
| 2003/0172929 | A1* | 9/2003 | Muellner | A61M 16/202 128/204.22 |
| 2004/0079359 | A1* | 4/2004 | Aylsworth | A61M 16/10 128/200.14 |
| 2007/0089796 | A1* | 4/2007 | Electra Brown | G05D 11/03 137/896 |
| 2013/0108715 | A1* | 5/2013 | Kobayashi | A61P 9/10 424/718 |
| 2014/0370125 | A1* | 12/2014 | De Villemeur | A61M 16/107 424/718 |
| 2016/0228670 | A1* | 8/2016 | Av-Gay | A61M 16/0057 |
| 2017/0182088 | A1* | 6/2017 | Dasse | A61K 31/506 |
| 2018/0177969 | A1* | 6/2018 | Yamamori | B01F 15/0429 |

FOREIGN PATENT DOCUMENTS

| | | | |
|---|---|---|---|
| JP | S57-156017 | 9/1982 | |
| JP | H1-219009 | 9/1989 | |
| JP | H2-003648 | 1/1990 | |
| JP | 2000-517311 | 12/2000 | |
| JP | 2011-184398 | 9/2011 | |
| JP | 2014-141536 | 8/2014 | |
| JP | 2017-197541 | 11/2017 | |
| JP | 2019-505343 | 2/2019 | |
| WO | 98/008523 | 3/1998 | |
| WO | WO-2012170843 A1 * | 12/2012 | ............. A61P 11/06 |
| WO | 2017/116776 | 7/2017 | |

OTHER PUBLICATIONS

Huiying Liu, et al., "Combination Therapy With Nitric Oxide and Molecular Hydrogen in a Murine Model of Acute Lung Injury", SHOCK / the Shock Society, 2015, vol. 43, No. 5, p. 504-511.

International Preliminary Report on Patentability of PCTJP2020009238, dated Sep. 23, 2021, 8 pages.

Sutherland, B. A. et al., "Inhalation Gases of Gaseous Mediators As Neuroprotectants for Cerebral Ischaemia," Current Drug Targets, 14, 2013, pp. 56-73, XP055694045.

Shinbo, T. et al., "Breathing nitric oxide plus hydrogen gas reduces ischemia-reperfusion injury and nitrotyrosine production in murine heart," American Journal of Physiology Heart and Circulatory Physiology, 305, 2013, pp. H542-H550, XP055189621.

Extended European Search Report issued for European Patent Application No. 20769508.1, dated Feb. 21, 2022, 5 pages.

* cited by examiner

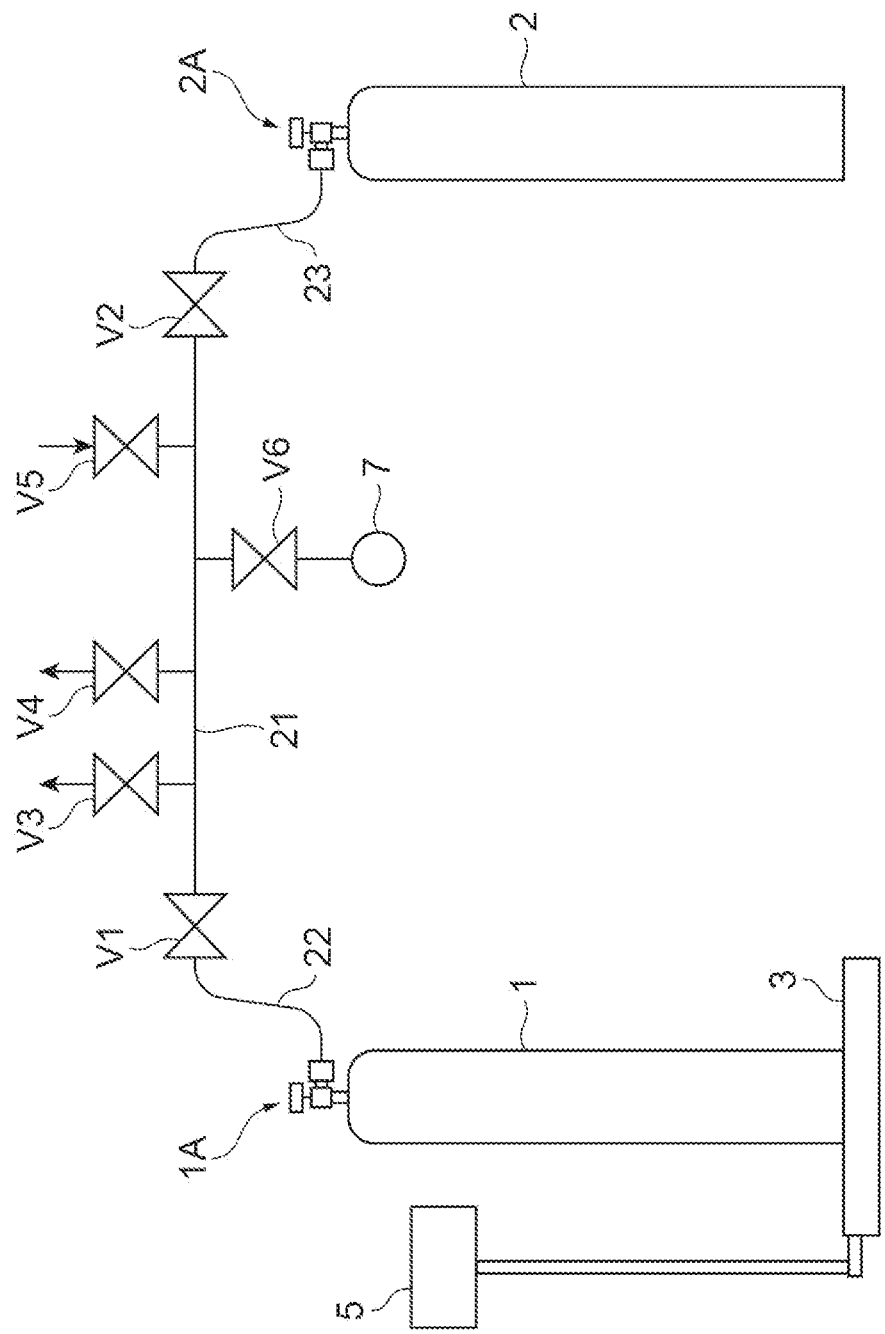

GAS PRODUCT, METHOD FOR PRODUCING SAME AND METHOD FOR PRODUCING MEDICAL INHALATION GAS

TECHNICAL FIELD

The present invention relates to a gas product, a method for producing the same, and a method for producing medical inhalation gas.

BACKGROUND ART

It has been reported that inhalation of a gas composition containing nitrogen monoxide, hydrogen, and oxygen can effectively reduce organ and tissue damage during ischemia-reperfusion (Patent Literature 1).

CITATION LIST

Patent Literature

Patent Literature 1: Japanese Unexamined Patent Publication No. 2011-184398

SUMMARY OF INVENTION

Technical Problem

In medical practice using a gas composition containing a combination of a plurality of kinds of gases as described in Patent Literature 1, it is necessary to strictly control the supply amount of each gas to administer the plurality of kinds of gases to a patient at the same time by inhalation. For that purpose, large-scale and expensive equipment and complicated operations are required. In order to further improve safety and accuracy of a medical treatment, it is desired that a plurality of kinds of gases can be administered by inhalation at the same time by a simpler method.

Therefore, an object of an aspect of the present invention is to provide a gas product that makes it possible to more simply perform a medical practice of simultaneously administering nitrogen monoxide, hydrogen, and oxygen by inhalation.

Solution to Problem

An aspect of the present invention relates to a gas product including: a gas container; and a gas composition filled in the gas container. The gas composition includes nitrogen monoxide, hydrogen, and an inert gas, and the concentration of the nitrogen monoxide is 20% by volume or less based on a volume of the gas composition.

Since the combination of the nitrogen monoxide and the hydrogen is a combination of a combustion-supporting gas and a flammable gas, it is generally considered difficult to stably store a mixed gas containing both for a long period of time. In particular, in the case of a medical gas, extremely high storage stability is required, such as a fluctuation range of the concentration of each gas within ±5% in one year. However, it is usually difficult to expect the mixed gas in which nitrogen monoxide and hydrogen coexist is such high to have such high storage stability. However, according to the findings of the present inventors, it has been found that when a concentration of nitrogen monoxide is 20% by volume or less, the gas composition containing nitrogen monoxide and hydrogen can be stably stored as a gas product, and the present invention has been completed.

According to the gas product, the gas composition can be stably stored in the gas container of the gas product for a long period of time. Further, by using the gas composition in the gas product according to the present invention, a medical practice of administering three kinds of gas, nitrogen monoxide, hydrogen, and oxygen to a patient at the same time by inhalation can be carried out only by controlling a supply of two kinds of gas, that is, the gas composition and a gas containing oxygen.

Another aspect of the present invention relates to a method for producing the gas product. The method includes in the following order: filling a gas container with a first raw material gas including nitrogen monoxide and an inert gas; further filling the gas container with a second raw material gas containing hydrogen and an inert gas; and further filling the gas container with an inert gas to form a gas composition containing the nitrogen monoxide, the hydrogen, and the inert gas, in which a concentration of the nitrogen monoxide is 20% by volume or less based on a volume of the gas composition. According to the method, the gas product can be produced efficiently and with high accuracy.

Still another aspect of the present invention relates to a method for producing a medical inhalation gas including nitrogen monoxide, hydrogen and oxygen. The method includes mixing the gas composition in the gas product with a gas containing oxygen. According to the method, it is possible to simply and efficiently produce a medical inhalation gas for performing a medical practice of administering three kinds of gases, that is, nitrogen monoxide, hydrogen, and oxygen to a patient at the same time by inhalation.

Advantageous Effects of Invention

According to one aspect of the present invention, there is provided a gas product that makes it possible to more simply perform a medical practice of administering nitrogen monoxide, hydrogen, and oxygen at the same time by inhalation. The gas product according to one aspect of the present invention can also have excellent storage stability for a long period of time without showing explosiveness in the gas composition to be filled.

BRIEF DESCRIPTION OF DRAWINGS

FIG. 1 is a schematic view showing an example of a filling device for producing a gas composition.

DESCRIPTION OF EMBODIMENTS

Hereinafter, some embodiments of the present invention will be described in detail. However, the present invention is not limited to the following embodiments.

A gas product according to an embodiment includes a gas container and a gas composition with which the gas container is filled. The gas composition is filled in the gas container to be stored and used. The gas container may be a pressure-resistant gas cylinder having a gas chamber. The gas chamber may have an inner wall surface made of stainless steel. The inner wall surface may be treated by physical polishing, chemical polishing, or electrolytic polishing from the viewpoint of preventing a metal on the inner wall surface from acting as a catalyst that promotes a reaction between nitrogen monoxide and hydrogen.

The gas composition according to an embodiment includes nitrogen monoxide, hydrogen, and an inert gas. By mixing the gas composition with a gas containing oxygen, a medical inhalation gas including nitrogen monoxide, hydrogen, and oxygen can be formed. That is, the gas product according to an embodiment is used for forming a medical inhalation gas including nitrogen monoxide, hydrogen, and oxygen. The medical inhalation gas is usually formed in a clinical site and immediately administered to a patient by inhalation. The medical inhalation gas can be used, for example, as a medicine for reducing ischemia-reperfusion injury.

In the gas composition according to an embodiment, a concentration of the nitrogen monoxide is 20% by volume or less based on a volume of the gas composition. When the concentration of the nitrogen monoxide is 20% by volume or less, the gas composition does not exhibit explosiveness, and also the gas composition can be stably stored as a gas product for a long period of time. From the same viewpoint and from the viewpoint of efficient formation of the medical inhalation gas, the concentration of the nitrogen monoxide may be 5% by volume or less, or 1% by volume or less, and may be 10 volume ppm or more, 50 volume ppm or more, 80 volume ppm or more, 100 volume ppm or more, or 200 volume ppm or more.

From the viewpoint described above, the concentration of nitrogen monoxide in the gas composition may be 10 volume ppm to 20% by volume, 50 volume ppm to 20% by volume, 80 volume ppm to 20% by volume, 100 volume ppm to 20% by volume, 200 volume ppm to 20% by volume, 10 volume ppm to 5% by volume, 50 volume ppm to 5% by volume, 80 volume ppm to 5% by volume, 100 volume ppm to 5% by volume, 200 volume ppm to 5% by volume, 10 volume ppm to 1% by volume, 50 volume ppm to 1% by volume, 80 volume ppm to 1% by volume, 100 volume ppm to 1% by volume, or 200 volume ppm to 1% by volume, based on the volume of the gas composition.

From the viewpoints of the stability of the gas composition and the efficient formation of the medical inhalation gas, the concentration of hydrogen is 0.1% by volume or more, 1% by volume or more 2% by volume or more, and may be 40% by volume or less, 10% by volume or less, or 4.7% by volume or less, based on the volume of the gas composition. From the viewpoint described above, the concentration of hydrogen may be 0.1% by volume to 40% by volume, 0.1% by volume to 10% by volume, 0.1% by volume to 4.7% by volume, 1% by volume to 40% by volume, 1% by volume to 10% by volume, 1% by volume to 4.7% by volume, 2% by volume to 40% by volume, 2% by volume to 10% by volume, or 2% by volume to 4.7% by volume, based on the volume of the gas composition.

The gas composition according to an embodiment may be a mixed gas including nitrogen monoxide and hydrogen and an inert gas as a balance. However, the gas composition may contain trace amounts of inevitable impurities. The inert gas may be a gas that does not substantially react with nitrogen monoxide and hydrogen. From an economic point of view, the inert gas may be nitrogen.

A total pressure of the gas composition according to an embodiment may be 0.1 MPa or more, or 10 MPa or more, mainly from the economic point of view. Furthermore, the total pressure of the gas composition may be required to be 15 MPa or less due to restrictions under the High Pressure Gas Safety Act. From the viewpoint described above, the total pressure of the gas composition may be 0.1 MPa to 15 MPa or 10 MPa to 15 MPa.

The gas product described above can be produced by, for example, a method including: in the following order: filling a gas container with a first raw material gas including a nitrogen monoxide and an inert gas; further filling the gas container with a second raw material gas containing hydrogen and an inert gas; and further filling the gas container with an inert gas to form a gas composition containing the nitrogen monoxide, the hydrogen, and the inert gas.

FIG. 1 is a schematic view showing an example of a filling device for producing a gas product according to an embodiment. The filling device shown in FIG. 1 includes: a pipe 21; a valve V1 and a valve V2 respectively mounted on both ends of the pipe 21; a pipe 22 connected to the valve V1; a pipe 23 connected to the valve V2; a valve V3, a valve V4, a valve V5, and a valve V6 which are connected to the pipe 21 at a position between the valves V1 and V2; a pressure gauge 7 connected to the valve V6; and a platform scale 3 disposed near the pipe 22. The pipes 21, 22, and 23 form a flow path for circulating a raw material gas and the like. From the side of the valve V1, the valve V3, the valve V4, the valve V6, and the valve V5 are connected to the pipe 21 in the following order.

A gas container 1 filled with the target gas composition is connected to the pipe 22 and placed on the platform scale 3. The gas container 1 has a container valve 1A. A gas container 2 filled with the raw material gas is connected to the pipe 23. The gas container 2 has a container valve 2A. The container valve 1A and the container valve 2A are provided to prevent flow between the gas chambers in the gas containers 1 and 2 and the outside (atmosphere). By replacing the gas container 2, the raw material gas containing different components can be sequentially supplied.

Temperatures of the raw material gas and the produced gas composition are usually −92° C. to 60° C. When the temperature is lower than −92° C., there is a possibility that nitrogen monoxide will liquefy. From the viewpoint of the High Pressure Gas Safety Act, the temperatures of the raw material gas and the produced gas composition may be 40° C. or lower.

The gas container 1 and the gas container 2 are connected via pipes 21, 22, and 23. The gas container 1 is filled with a target gas composition by supplying the raw material gas from the gas container 2. The pipes 22 and 23 may be flexible high pressure pipes.

A pipe for supplying a high-pressure inert gas (for example, nitrogen gas) is connected to the valve V5. When the valve V5 is opened, an inert gas as a diluting gas is supplied to the pipe 21. The valve V4 is connected to a detoxifying device. When the valve V4 is opened, the gas existing in the pipe 21 at a pressure equal to or higher than the atmospheric pressure is discharged to the detoxifying device until the pressure reaches the atmospheric pressure. A pipe for discharging a gas to the vacuum pump is connected to the valve V3. When the valve V3 is opened, an inside of the pipe 21 can be made almost vacuum.

The platform scale 3 has a weight indication part 5. The platform scale 3 may be a so-called load cell type platform scale. A filling amount of each raw material gas is adjusted by filling the gas container 1 with the raw material gas while measuring the weight of the gas container 1 with the platform scale 3. The weight of each raw material gas forming the produced gas composition can be calculated in advance.

The pipe 22 is connected to the container valve 1A of the gas container 1. The gas container 1 is sealed by a container valve 1A. The inside of the gas container 1 may be decompressed in advance. Next, the container valve 2A of the gas container 2 filled with a first raw material gas M1 containing nitrogen monoxide and an inert gas is connected to the pipe 23. The first raw material gas M1 may contain nitrogen monoxide having a concentration of about 1 to 20 times the concentration in the produced gas composition.

Next, in order to discharge the air in the pipe, the valve V1, the valve V2, and the valve V3 are opened, the valve V4 and the valve V5 are closed, and insides of the pipes 21, 22, and 23 are made almost vacuum with the vacuum pump connected to the valve V3. After closing V3, in order to dilute slightly remaining oxygen, the valve V5 is opened and nitrogen gas is supplied to the pipes 21, 22 and 23 up to a pressure of about 1 MPa. The valve V5 is closed, the valve V4 is opened, and nitrogen gas is discharged up to near the atmospheric pressure. After closing the valve V5, the valve V3 is opened, and the insides of the pipes 21, 22, and 23 are made almost vacuum again by the vacuum pump. These operations are repeated several times to dilute and discharge the remaining oxygen. Finally, the valve V3 is closed in a state where the insides of the pipes 21, 22, and 23 are made almost vacuum by opening the valve V3.

After that, the container valve 2A is opened and closed, and the first raw material gas M1 is introduced into the pipes 21, 22, and 23 until an indication of the pressure gauge 7 connected to the pipe 21 reaches 0.5 MPa to 2 MPa above the internal pressure of the gas container 1. The valve V1 is closed and the container valve 1A is opened. At this time, the weight indication part 5 of the platform scale 3 is reset to zero.

After opening the valve V1 and confirming that the indication of the pressure gauge 7 is lowered, the container valve 2A is opened and closed, and the gas container 1 is filled with the first raw material gas M1 having a weight calculated in advance. After filling, the container valve 1A is closed. The indicated pressure of the pressure gauge 7 at this time is recorded.

The first raw material gas M1 remaining in the pipes 21, 22, and 23 is discharged up to near the atmospheric pressure by opening the valve V4. After discharging, the valve V5 is opened to supply the inert gas to the pipes 21, 22, and 23 up to a pressure of about 1 MPa. Thereafter, the valve V5 is closed, the valve V4 is opened, and the inert gas is discharged up to near the atmospheric pressure. Next, the valve V4 is closed, the valve V3 is opened, and the insides of the pipes 21, 22, and 23 are made almost vacuum by the vacuum pump. These operations are repeated several times to dilute and discharge the remaining nitrogen monoxide gas. Thereafter, the valve V5 is opened and closed to introduce an inert gas so that the insides of the pipes 21, 22, and 23 are at atmospheric pressure or higher. After closing the valve V1 and removing the pipe 22 from the container valve 1A, the weight of the gas container 1 is measured and recorded.

Subsequently, in a state where the valve V2 closed, the gas container 2 is replaced with a container filled with a second raw material gas M2 containing hydrogen and an inert gas. The container valve 1A of the gas container 1 is connected again to the pipe 22. The second raw material gas M2 may contain hydrogen having a concentration of about 1 to 20 times the concentration in the produced gas composition.

After diluting and discharging the oxygen remaining in the pipes 21, 22, and 23 by the same operations as described above, the valve V3 is closed in a state where the insides of the pipes 21, 22, and 23 are made almost vacuum by opening the valve V3.

Next, the container valve 2A is opened and closed, and the second raw material gas M2 is introduced into the pipes 21, 22, and 23 until the indication of the pressure gauge 7 connected to the pipe 21 reaches 0.5 MPa to 2 MPa above the internal pressure of the gas container 1. The valve V1 is closed and the container valve 1A is opened. At this time, the weight indication part 5 of the platform scale 3 is reset to zero.

After opening the valve V1 and confirming that the indication of the pressure gauge 7 is lowered, the container valve 2A is opened and closed, and the gas container 1 is filled with the second raw material gas M2 having a weight calculated in advance. After filling, the container valve 1A is closed. The indicated pressure of the pressure gauge 7 at this time is recorded.

The second raw material gas M2 remaining in the pipes 21, 22, and 23 is discharged up to near the atmospheric pressure by opening the valve V4. After discharging, the valve V5 is opened to supply the inert gas to the pipes 21, 22, and 23 up to a pressure of about 1 MPa. Thereafter, the valve V5 is closed, the valve V4 is opened, the inert gas is discharged up to near the atmospheric pressure. Then, the valve V4 is closed, the valve V3 is opened, and the insides of the pipes 21, 22, and 23 are made almost vacuum by the vacuum pump. These operations are repeated several times to dilute and discharge the remaining hydrogen gas. Thereafter, the valve V5 is opened and closed to introduce an inert gas so that the insides of the pipes 21, 22, and 23 are at atmospheric pressure or higher. After closing the valve V1 and removing the pipe 22 from the container valve 1A, the weight of the gas container 1 is measured and recorded.

Subsequently, the container valve 1A of the gas container 1 is connected again to the pipe 22. After diluting and discharging the oxygen remaining in the pipes 21, 22, and 23 by the same operations as described above, the valve V3 is closed in a state where the insides of the pipes 21, 22, and 23 are made almost vacuum by opening the valve V3.

Next, the valve V5 is opened and closed, and the inert gas is introduced into the pipes 21, 22, and 23 until the indication of the pressure gauge connected to the pipe 21 reaches 0.5 MPa to 2 MPa above the internal pressure of the gas container 1. The valve V1 is closed and the container valve 1A is opened. At this time, the weight indication part 5 of the platform scale 3 is reset to zero.

After opening the valve V1 and confirming that the indication of the pressure gauge 7 is lowered, the valve V5 is opened and closed, and the gas container 1 is filled with the inert gas having a weight calculated in advance. After filling, the container valve 1A is closed. The indicated pressure of the pressure gauge 7 at this time is recorded.

Thereafter, the valve V4 is opened, and the inert gas remaining in the pipes 21 and 22 is discharged up to near atmospheric pressure. The valve V5 is opened and closed, and nitrogen gas having the atmospheric pressure or higher is introduced into the pipe 21. In this state, the pipe 22 is removed from the container valve 1A. The weight of the gas container 1 at this time is measured and recorded.

By the above operations, a filled gas container filled with the gas composition can be obtained, and the filled gas container can be used as a gas product. A temperature at which the gas product (filled gas container) is stored is usually −92° C. to 60° C. When the temperature is lower than −92° C., there is a possibility that nitrogen monoxide will liquefy. From the viewpoint of the High Pressure Gas Safety Act, the storage temperature may be 40° C. or lower.

A medical inhalation gas including nitrogen monoxide, hydrogen, and oxygen can be produced using the gas product described above. The method for producing the medical inhalation gas according to an embodiment includes mixing the gas composition in the gas product described above with a gas containing oxygen.

In the method, the medical inhalation gas is obtained, for example, by supplying the gas composition from the gas product described above and supplying a gas containing oxygen and mixing the supplied gases in a clinical site. The mixing of the gas composition with the gas containing oxygen is preferably performed immediately prior to inhalation by the patient.

EXAMPLES

Hereinafter, the present invention will be described in more detail with reference to examples. However, the present invention is not limited to these examples.

1. Explosion Test of Gas Composition

A gas composition containing nitrogen monoxide, hydrogen, and nitrogen having the concentrations shown in Table 1 below was introduced into an explosive cylinder having an inner diameter of 55 cm and a height of 100 mm and equipped with a discharge electrode and a cork lid. A safety cover surrounding the explosive cylinder was closed and a spark discharge was generated between the electrodes. It was determined that there was an explosion in a case where the lid of the explosive cylinder flew, and that there was no explosion in a case where the lid of the explosive cylinder did not fly. The same test was performed three times for each of the gas compositions of Examples 1 to

TABLE 1

| | Concentration/% by volume | | |
|---|---|---|---|
| | NO | $H_2$ | $N_2$ |
| Example 1 | 5 | 40 | 55 |
| Example 2 | 20 | 20 | 60 |
| Example 3 | 10 | 20 | 70 |

As a result of the explosion test, it was confirmed that none of the gas compositions exploded. From the result, it was confirmed that a limit concentration of nitrogen monoxide at which the gas composition containing nitrogen monoxide, hydrogen gas, and an inert gas can exhibit explosiveness exceeds 20% by volume. From the fact, it can be said that the gas composition containing nitrogen monoxide, hydrogen gas, and an inert gas does not substantially exhibit explosiveness regardless of the hydrogen concentration as long as the concentration of the nitrogen monoxide is 20% by volume or less. In addition, it can be said that even a gas product obtained by filling the gas container with the gas composition does not substantially exhibit explosiveness.

2. Stability Test of Gas Composition (1) $NO/N_2$ Gas

Five gas cylinders made of tempered manganese steel were prepared. Each gas cylinder was filled with a gas composition including about 9 volume ppm of nitrogen monoxide and nitrogen. The nitrogen monoxide concentration 2 days after filling was measured, and a rate of increase or decrease from an initial stage (at the time of filling) was calculated. As shown in Table 2, the concentration of nitrogen monoxide decreased at a relatively large rate of about 3% to 4%.

TABLE 2

| | NO concentration/volume ppm | | Rate of increase |
|---|---|---|---|
| No. | Initial stage | 2 days after | or decrease/% |
| 1 | 9.01 | 8.57 | −4.9 |
| 2 | 9.03 | 8.78 | −2.8 |
| 3 | 9.01 | 8.77 | −2.7 |
| 4 | 9.01 | 8.62 | −4.3 |
| 5 | 9.02 | 8.75 | −3.0 |

(2) $NO/H_2/N_2$ Gas

Three gas cylinders made of tempered manganese steel were prepared. Each gas cylinder was filled with a gas composition including about 144 volume ppm of nitrogen monoxide, 3.5% by volume of hydrogen, and nitrogen as a balance. Nitrogen monoxide concentrations were measured 1 month, 6 months, and 12 months after filling. The rate of increase or decrease in the nitrogen monoxide concentration after 12 months from the initial stage (at the time of filling) was calculated. As shown in Table 3, in a case of the gas composition containing nitrogen monoxide, hydrogen, and an inert gas, the concentration of nitrogen monoxide was stably maintained for a long period of one year. From the fact, it can be said that the gas product obtained by filling the gas container with the gas composition can be stably stored for a long period of time.

TABLE 3

| | NO concentration/volume ppm | | | | Rate of increase |
|---|---|---|---|---|---|
| No. | Initial stage | After 1 month | After 6 months | After 12 months | or decrease after 12 months/% |
| 1 | 144.2 | 144.3 | 143.5 | 144.3 | −0.1 |
| 2 | 144.0 | 144.4 | 143.1 | 143.2 | 0.6 |
| 3 | 144.8 | 145.2 | 143.9 | 143.8 | 0.7 |

REFERENCE SIGNS LIST

1: Gas container, 1A: Container valve, 2: Gas container, 2A: Container valve, 21, 22, 23: Pipe, 3: Platform scale, 5: Weight indication part, 7: Pressure gauge, V1, V2, V3, V4, V5, V6: Valve.

The invention claimed is:

1. A method for producing a gas product comprising:
a gas container; and
a gas composition filled in the gas container;
wherein the gas composition consists of nitrogen monoxide, hydrogen, and an inert gas, and optionally trace impurities;
the gas product being useful for forming a medical inhalation gas comprising nitrogen monoxide, hydrogen, and oxygen by mixing the gas composition with a gas comprising oxygen, the method comprising, in the following order:
filling the gas container with a first raw material gas comprising nitrogen monoxide and a first inert gas;
further filling the gas container with a second raw material gas comprising hydrogen and a second inert gas; and
further filling the gas container with a third inert gas to form the gas composition containing the nitrogen monoxide, the hydrogen, and the inert gases, a concentration of the nitrogen monoxide being 20% by volume or less based on a volume of the gas composition, and a concentration of the hydrogen being 0.1% by volume or more and 10% by volume or less.

2. The method of claim 1, wherein the first inert gas, the second inert gas and the third inert gas are composed of a same inert gas.

* * * * *